United States Patent
Shafer

(10) Patent No.: US 7,033,761 B2
(45) Date of Patent: Apr. 25, 2006

(54) EXPRESSION MINIARRAYS AND USES THEREOF

(76) Inventor: David A. Shafer, 245 Danbury La., Atlanta, GA (US) 30327

(*) Notice: Subject to any disclaimer, the term of this patent is extended or adjusted under 35 U.S.C. 154(b) by 0 days.

(21) Appl. No.: 09/992,516

(22) Filed: Nov. 14, 2001

(65) Prior Publication Data

US 2002/0074342 A1    Jun. 20, 2002

Related U.S. Application Data

(60) Provisional application No. 60/248,247, filed on Nov. 14, 2000.

(51) Int. Cl.
*C12Q 1/68* (2006.01)

(52) U.S. Cl. .................. 435/6; 435/4; 435/287.2; 435/287.3; 435/DIG. 17; 536/22.1

(58) Field of Classification Search .............. 435/6, 435/4, 287.2, 287.3, DIG. 17; 536/22.1

See application file for complete search history.

(56) References Cited

U.S. PATENT DOCUMENTS

| 5,807,522 A | 9/1998 | Brown ................... 422/50 |
| 6,040,138 A * | 3/2000 | Lockhart et al. ............ 435/6 |
| 6,063,339 A * | 5/2000 | Tisone et al. ............. 422/67 |
| 6,083,763 A | 7/2000 | Balch .................. 436/518 |
| 6,101,946 A | 8/2000 | Martinsky .............. 101/494 |
| 6,143,252 A | 11/2000 | Haxo .................. 422/131 |
| 6,248,521 B1 * | 6/2001 | Van Ness et al. ........... 435/6 |
| 6,429,027 B1 * | 8/2002 | Chee et al. ............. 436/518 |

OTHER PUBLICATIONS

Lange et al, Ger. Offen. (1998), abstract only.*
Little et al , Anal.chem. 1997, 69, 4540-46.*

* cited by examiner

*Primary Examiner*—T. D. Wessendorf
(74) *Attorney, Agent, or Firm*—Benjamin Aaron Adler

(57) ABSTRACT

The present invention provides methods and devices for making new and inexpensive miniarrays suitable for gene expression analysis. Also provided herein are methods of diagnosis for specific tissue or condition using specialized diagnostic miniarrays that exhibit specific visual pattern as diagnostic readout.

9 Claims, 7 Drawing Sheets

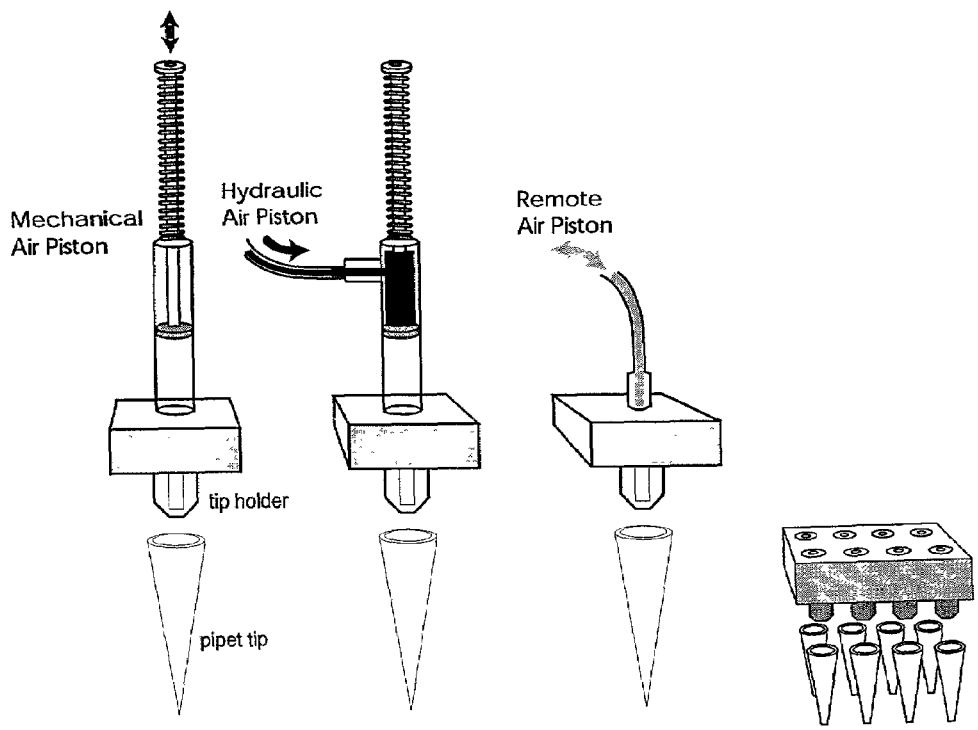
Fig. 1A  Fig. 1B
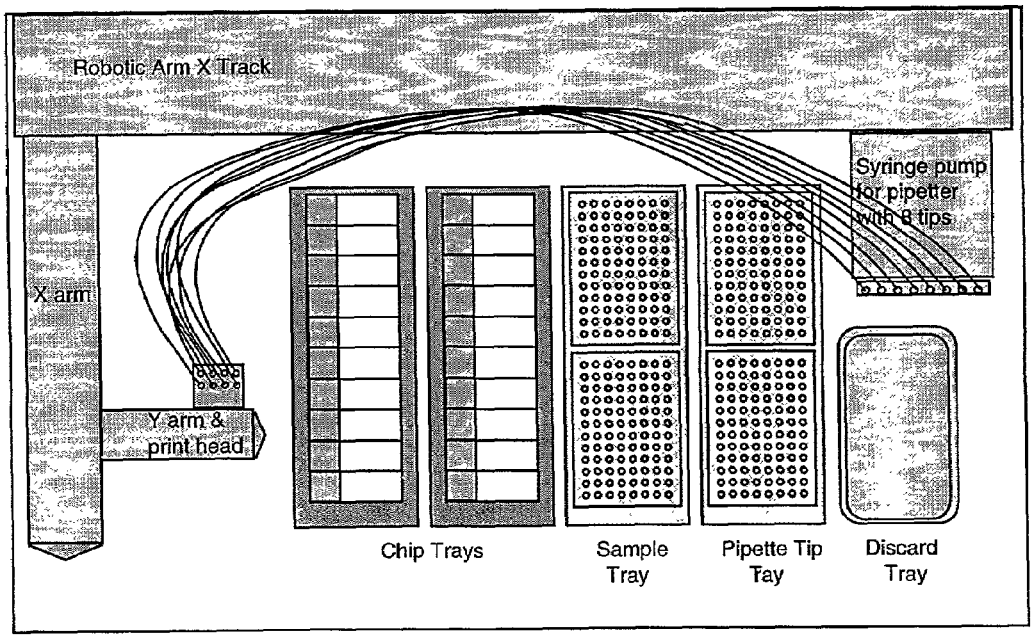
Fig. 2

Black dots represent the first print distribution with a 8 tip printhead having 2 rows of four tips. 50 nL spots similarly dispensed would achieve ~2500 gene spots in the same printing area.

Step 1: Copy target segment by RT with poly-T primer plus GeneTAG linker
remove mRNA
Step 2:: Ligate Random Adapter forming second GeneTAG linker/primer site
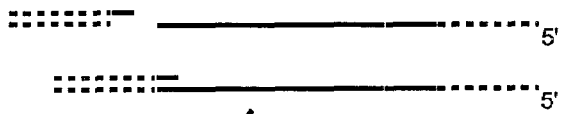
purify
Double Linker WRAP Probes suitable for PCR amplification
Step 3: PCR amplify
PCR with global primers
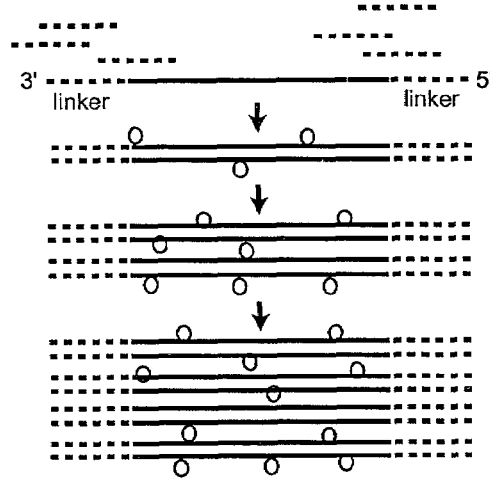
PCR with labeled global primers (ChipTAGs)
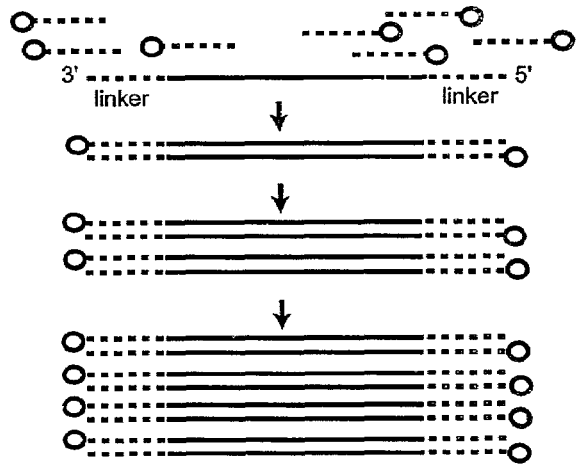
Fig. 4

Hand spotted miniarray test
with P-10 micropipetter and
Cy3 and Cy5 labeled samples
on polylysine coated slides
spots ~3 mm CTC Upper Row
    600 nL, 400 nL, 200 nL
    1.35mm, 1.2mm, .78 mm
Mid Row
    800 nL, 400 nL, 200 nL
    1.78mm, 1.2mm, .78mm
Lower Row
    800 nL, 400 nL, 200 nL
    1.78mm, 1.2mm, .78mm Using intermediate half-probes ligated together on the target sequence:
Step 1: bind and ligate paired half-probes
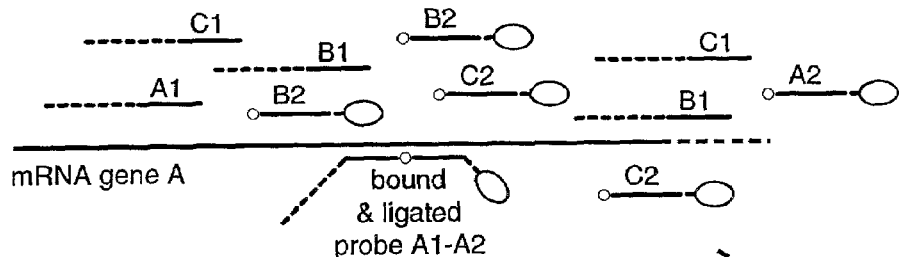
Step 2: capture and wash off unbound probes
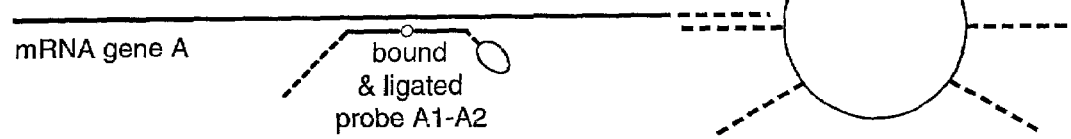
Step 3: degrade RNA
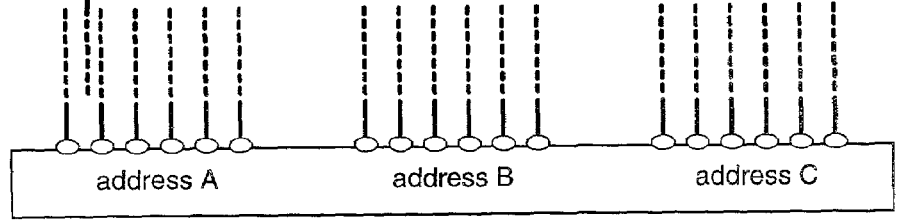
resulting probe set = target set
Step 4: capture probe and reporter to matching array address
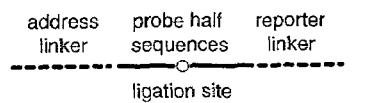
address A        address B        address C
Alternate Probe form: Reporter bound separately to reporter linker:
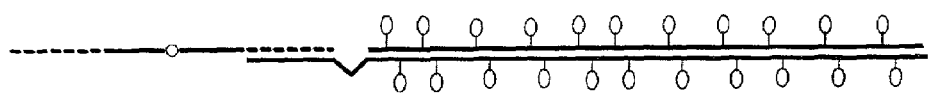
Fig. 9

EXPRESSION MINIARRAYS AND USES THEREOF

CROSS-REFERENCE TO RELATED APPLICATION

This non-provisional patent application claims benefit of provisional patent application U.S. Ser. No. 60/248,247, filed Nov. 14, 2000, now abandoned.

BACKGROUND OF THE INVENTION

1. Field of the Invention

The present invention relates generally to the field of gene expression array technology. More specifically, the present invention relates to the making and uses of larger format miniarrays that have similar analytic and diagnostic values as expression microarrays.

2. Description of the Related Art

Prior to the development of high density expression microarrays, low density nucleic acid hybridization arrays were commonly manufactured by hand or with limited automation. These low density nucleic acid hybridization arrays were used to detect concentration or sequence differences between samples or to simultaneously detect and compare complex analyte samples containing unknown products or a mix of multiple products. Genetics research has routinely employed such hand-made arrays commonly known as "dot blots", "slot blots" or "reverse dot blots".

With these large format macroarrays, microliter quantities of various reagents or test samples are manually pipetted or vacuumed onto a porous membrane in defined locations to create an array or grid of such products against which a mix of test samples or probes is applied. For such macroarray assays, the DNAs spotted on the arrays are typically bound to the membrane by UV or microwave radiation, and then the membrane is coated or immersed in milliliter quantities of analyte sample under controlled hybridization conditions. After hours of hybridization and washing, and depending on the labeling employed, the results are typically rendered visible by either x-ray film, staining, or enzymatic color reactions. Since these procedures are largely manual, usually only one array is made at a time and the spot density rarely exceeds a few dozen per array. Such macroarray formats are unsuitable for repetitive applications or high throughput, high-density analyses.

Higher density hybridization arrays have been made with a block of pins that were dipped into multiple wells at a time and then spotted on a membrane in an interspersed pattern Lehrach et al., 1990). However, this approach remains largely a manual procedure with variation in spot size and volume, and limitations on reproducible manufacture.

Higher density arrays of oligonucleotide probes were first developed by Fodor et al. (1991) and Pirrung et al. (U.S. Pat. No. 5,143,854), wherein nucleic acid segments were synthesized in place at the different array locations. These methods involved complex methods and equipment, and the probes generated were short (20 to 25 bases). A related method was described by Southern et al. (1992). Oligonucleotide arrays have also been described by Khrapko, et al. (1991) in which DNA was hand spotted on a polyacrylamide gel with a micropipetter. However, oligonucleotide arrays were principally developed for detecting DNA sequences and only recently were they reapplied to make gene expression microarrays similar to cDNA-based microarrays (U.S. Pat. No. 6,040,138). In the past year. several biotechnology companies have begun making microarrays and sample components based on synthetic, long oligonucleotides suitable for printing.

The recent development of cDNA based expression microarrays provides a ready means to simultaneously assess the relative expression of hundreds or thousands of different genes from cellular or tissue samples (Schena et al., 1995, 1996; Shalon et al., 1998; DoRlsl et el., 1996; Haller at al., 1997; Khan at al., 1998, 1999). These analyses were accomplished by first preparing miniature grids or arrays on membranes or coated glass substrates by spotting robotically small but dense cDNA samples of individual genes in a two dimensional pattern. Then, the mRNA transcripts of a sample were copied using reverse transcriptase, a poly-T primer and labeling agents to create a pool of cDNA based probes. These labeled probes were then hybridized to their respective gene spots in the expression microarray in order to detect and determine the relative frequency of each transcript in the original sample. These expression microarrays, which are also commonly called cDNA chips, DNA chips or BloChips, can also be manufactured from gene specific synthetic oligonucleotides that likewise were created or distributed on an array in a two dimensional pattern (U.S. Pat. No. 5,445,934, U.S. Pat. No. 5,800,992 and U.S. Pat. No. 8,040,138).

In high density gene expression microarrays, picoliter quantities of cDNA-based reagents are deposited in close proximity on solid supports, with assay spots typically 75 to 150 microns in diameter and with center to center (CTC) spacing of 100 to 375 microns. Most of these devices spot the microarrays with a row of fine pins that load and dispense by capillary action. The pins may be solid, split, pinched like a quill pen, scored with channels, or encircled with a floating ring to hold larger quantities of sample per loading and to allow dispensing a defined smaller sample per spot. Typically, 0.5–2.5 nanoliter quantities are dispensed by capillary action as the spring-loaded pin is brought into contact with the substrate surface (U.S. Pat. No. 6,110,426). Alternatively, piezoelectric or inkjet technology has been employed to load larger quantities and to dispense small microdroplets by electronic activation without contacting the surface. Gamble at al. reported a piezoelectric or thermally activated pulse Jetting device where the tip of the print head or pulse jet can dispense microdroplets of about 0.5 nanoliters or less to achieve spots on a chip spaced 80 microns CTC with 15 microns between spots (U.S. Pat. No. 6,001,309).

The technologies described above were intentionally developed to create very high-density microarrays with thousands of different gene specific assay spots per chip. The need to miniaturize these expression arrays is due to the fact that mRNA samples available for such analyses are frequently quite limited and methods to amplify the sample products are inefficient. Moreover, hybridization kinetics is very slow in large volumes of hybridization solution. Therefore, in order to assess the expression of hundreds or thousands of genes per sample, the spot density of the array format must be greatly increased without increasing the size dimensions of the array, the volume of hybridization solution, the time of hybridization, or the overall sensitivity for detecting each analyte in the sample. However, the development of these miniaturized, high density arrays comes at great cost and limitations, since the equipment required is complex and delicate, the pin heads or jets must be thoroughly washed and cleaned between sample loadings, specialized temperature and humidity controls and enclosures are required, and complex robotic procedures must be programmed for each run. Very high-density microarrays must also employ dust free "clean room" conditions and equipment that parallel the specialized facilities required for the manufacture of computer chips. Such miniaturization also requires the use of very expensive, specialized labeling reagents. Moreover, while these expression microarrays allow a high throughput overview and assessment of the relative frequency of different gene transcripts in a sample, these methods are limited by significant deficiencies in quantification and sensitivity (DeRisi et al., 1996; Duggan et al., 1999; Rajeevan et al., 1999).

One approach to improve chip detection would be to amplify mRNA derived probes by the polymerase chain reaction (PCR) or related enzymatic methods. However, effective multi-analyte amplification typically requires the provision of at least one unique primer for each type of gene product amplified, and commonly available PCR procedures such as RT-PCR and multiplex PCR have only been used successfully to amplify a limited number of the gene products in a sample (U.S. Pat. No. 5,807,680). In methods such as differential display or other older procedures that are used to explore expression differences, global amplification methods have been employed based upon using simple arbitrary primers, hexamers or various random primer constructs instead of unique primers to amplify DNA or RNA. Inconsistency of these methods renders them useful only for identifying unusual or novel gene expression products, and they have not been devised or employed for use with expression microarrays or DNA chip analyses (Liang et al., 1993; Mou et al., 1994; Welsh et al., 1990; U.S. Pat. Nos. 5,262,311; 5,665,547; 5,580,726; 5,104,792; 5,789,206; 5,882,856).

The prime difficulty with many of these amplification methods stems from the use of short arbitrary or random primers mat can give variable results from gene to gene under different temperature and hybridization conditions such that they are unsuitable for repeated diagnostic analyses. Even RT-PCR or multiplex PCR methods which employ unique primers can produce semi-quantitative rather than quantitative results because different primer sets vary considerably in efficiency. Moreover, kinetic factors favor copying the smaller and more abundant products in these methods. Therefore, some products may not amplify well, and rare or down-regulated transcripts may be under-represented (Khan et al., 1999). Additionally, mammalian mRNA samples include very large gene transcripts 6 to 12 thousand nucleotides long that cannot be amplified reliably by routine PCR methods. Consequently, global PCR amplification of a pool of mRNA-derived cDNA probes has not been attempted or successfully accomplished with DNA chip or expression microarray analyses. Based on the above reasons, currently available exponential amplification methods cannot be validly applied to multi-analyte gene expression analysis.

Less robust linear amplification methods have been developed and employed for chip analyses by adding a RNA polymerase promoter to the end of the poly-T primer used for RT. However, such amplification is incremental and finite, with a typical duplication of 20–60 copies, and the amplified products it produces are antisense RNAs which are degradable (Philips at al., 1996; U.S. Pat. Nos. 5,972,607; 5,716,785). Wang at al. (U.S. Pat. No. 5,932,451) refined such methods to allow asymmetrical amplification of double stranded cDNA made from a mRNA sample. However, this amplification method is also limited in the number of copies typically made from a sample (only 68 fold duplication demonstrated).

Thus, prior art regarding gene expression arrays is deficient in methods and instruments to amplify a test sample effectively, to create and analyze arrays easily and reliably, and to provide less costly arrays that possess equivalent or improved analytic and diagnostic value. The present invention fulfills this long-standing need and desire in the art.

SUMMARY OF THE INVENTION

The present invention provides methods and devices for a new, inexpensive miniarray suitable for gene expression analysis. Mechanized large format miniarrays of low or high density was developed due to gains in sensitivity resulted from methods of signal amplification and probe amplification disclosed herein. In contrast to the making of very small, high-density expression microarrays which require: (1) very expensive spotters that deposit picoliter volumes per spot with delicate, miniaturized pins or inkjets; (2) special dust free and humidity conditions during manufacture, and (3) high resolution fluorescent image scanners for analysis, the present invention creates simpler, less expensive mini-format arrays based on employing automated pipetters which can reliably deposit nanoliter volumes of analyte specific reagents in a known grid pattern on solid or membrane supports.

The miniarray of the present invention is also designed to employ disposable pipette tips that can be ejected and replaced to avoid tip cleaning and contamination problems between loading of samples. The spotter apparatus of the present invention operates printing, loading, tip changing and other operations mechanically or robotically in order to facilitate miniarray manufacture. Fabrication of this miniarray is less sensitive to dust or humidity conditions, and arrays with larger spots can be analyzed with simpler, lower resolution scanners. The miniarray devices and methods disclosed herein are more refined than manually fabricated macroarrays, and the miniarrays provide economic, high quality expression assays that exhibit diagnostic value comparable or equivalent to the more expensive, high-density, microarray assays.

The devices and methods disclosed herein also provide new diagnostic miniarray configurations customized to different diseases or conditions. The arrays can be arranged or organized to form and display simple visual patterns that indicate the presence of the disease or condition. In one embodiment, the miniarray will generate a simple identifying pattern such as a "stoplight" pattern showing clusters of genes that are labeled "red", "yellow" and "green", indicating the predicted presence of gene activity levels that are up-regulated, unchanged, or down-regulated, respectively, in the disease or condition under examination. In another embodiment of the present invention, the pattern will be created within the computer program governing the analysis and display of the miniarray. In still another embodiment, the pattern will be spotted on the miniarray in the form of addressable probe binding locations. A probe set resulted from interaction with target sample in solution hybridization will then bind to the miniarray according to the preset pattern.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 1 shows a perspective elevational view of the pipette-based spotting devices.

FIG. 1A shows a mechanically operated pipetter, a hydraulic pipetter, and an air driven pipetter operated remotely by microtubing. The hydraulic or air driven pipetters are typically actuated by stepper motor-driven syringe pumps.

FIG. 1B shows an elevational view of an 8 tip printhead.

FIG. 2 shows a diagrammatic top view of a robotic working platform in combination with the above spotter print head for producing miniarrays. The print head contains two rows of four pipetters. Actuators such as stepper motor-activated syringe pumps are depicted with microtubing going to the printhead, and the print head is mounted upon a robotic arm which moves laterally and vertically in relation to the working platform. The platform contains stations or regions for holding array substrates to be spotted, one or more 96 well or 384 well plate with reagent samples, one or more racks of disposable pipette tips, and a discard tray. A printing operation proceeds sequentially in a repeated circular pattern starting from loading of pipette tips, loading of reagent samples, first printing pass on the substrates, and discarding of used pipette tips, followed by a repeat of this four step pattern until the miniarrays are fully printed.

FIG. 4 shows the processing of normal or disease specific tissue to yield mRNA samples and to convert those samples to exponentially amplified DNA based WRAP-Probes. The primary steps depicted are 1) reverse transcription to copy the mRNA and to affix a first linker sequence, 2) binding a random adapter to the 3' end of the first strand cDNA probes by ligation to affix a second linker sequence, and 3) employing primers complementary to the linkers to globally amplify the probe set. The number of copies of each probe is essentially proportional to the number of copies of gene transcripts in the original tissue sample. Exponential amplification allows the generation of up to a million probe copies in about 20 cycles of the modified PCR procedure. The probes from different tissues are separately prepared to allow two color labeling, either during amplification using labeled global primers called ChipTAGs, or via the binding of labeled GeneTAGs to the linker ends of the probes after hybridization.

FIG. 9 shows an alternate embodiment of the addressable diagnostic miniarray wherein the intermediate probes comprise pairs of matching half probes. The half probes bind to adjacent sites on each target and are ligated together after binding to produce a set of joined probes that have both a signaling component and a sequence tail corresponding to a miniarray sequence address. The ligation step ensures more accurate targeting and the two-part probes are easier to manufacture compared to a single long intermediate probe.

DETAILED DESCRIPTION OF THE INVENTION

Figure 3:
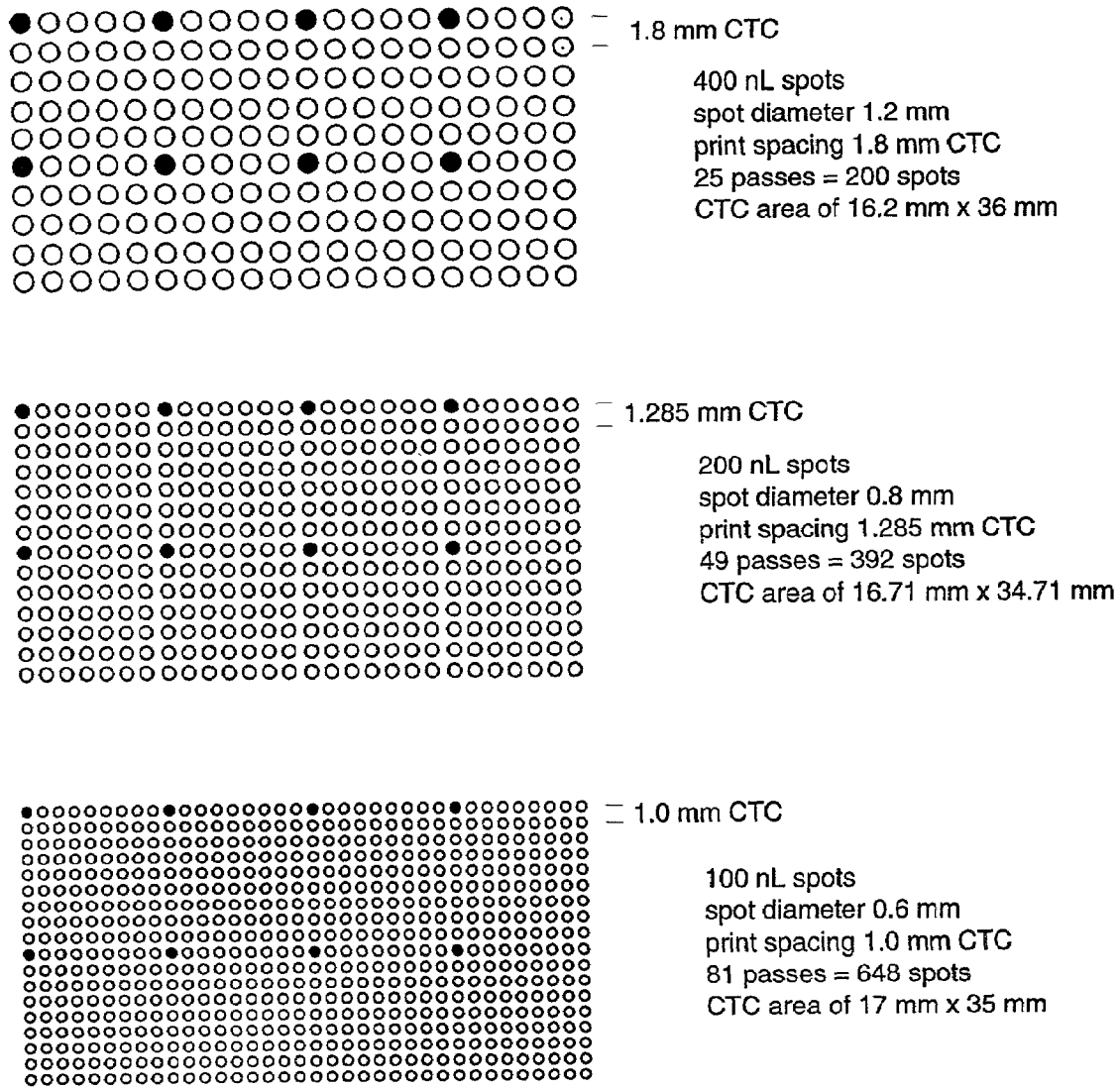
FIG. 3 shows variable density miniarray printing patterns based upon a print head containing 8 pipetters arranged in two rows of four pipetters with the tips spaced 9 mm CTC. The density of the printing is proportional to the size of the spots dispensed and the number of interspersed printings made with the same print head within the spaces between the first printing spots in the miniarray.

As used herein, the term "haptens" refers to indirect binding or labeling reagents that are incorporated or appended to probes. These haptens bind specifically to other molecules by biochemical or immunological affinity.

As used herein, the term "not substantially complementary" means that the oligonucleotide is not sufficiently complementary to hybridize with another strand of polynucleotide.

As used herein, the terms "GeneTAG" refers to linear generic reporter molecules with generic linkers.

As used herein, the term "ChipTAG" refers to small multifunction GeneTAGs constructed of synthetic oligonucleotides or other polynucleotides that can also serve as a RT primer, a PCR primer, a linker or a multi-linker.

As used herein, the term "linker" refers to single stranded nucleotide segment that is not complementary to the target sequence and that provides means to bind probe and reporter elements together.

As used herein, the term "multi-linker" refers to polynucleotide or complex of polynucleotides that self assemble and that provide a probe linker and two or more reporter linkers.

As used herein, the term "WRAP-Probe" refers to a DNA-based probe containing or affixed with linkers on one or both ends to bind generic reporters.

As used herein, the terms "addressable miniarray" refers to miniarrays that are spotted with binding elements that are not substantially complementary to the target sample and that create a series of either individual addresses or clusters of general addresses distributed on the array in known locations. The binding elements employed are generally synthetic polynucleotides or artificial DNAs creating an address sequence, or alternatively, affinity ligands such as avidin or antibodies that respectively bind biotin or various haptens affixed to the gene-specific probes.

The present invention provides a system of delivering small volumes of reagent solutions in a defined distribution pattern on a solid or membrane support in order to form miniarrays for uses in multi-analyte biological assays. Miniarrays disclosed herein are particularly useful for assessing gene expression profiles based on spotting cDNA or synthetic oligonucleotide samples.

In contrast to miniaturized printing technology such as capillary pin, piezoelectric or inkjet dispensers required for microarray formation, the present invention creates miniarrays by using much simpler, air-driven pipetter technology which can deliver nanoliter quantities of reagent solution. By shifting to low density or larger format miniarrays, the development and use of low-resolution scanners is likewise enabled as contrasted with the present need for scanning microarrays with confocal laser microscopy and/or other high resolution detectors. In addition, such low density or large format miniarrays further enable the use of less sensitive labeling agents such as simple colored dyes as compared to the present need for expensive, nonpermanent fluorescent labeling agents. This new miniarray instrument format enables ready customization of chips for the research and diagnostics market, eliminates problems of variation and expenses associated with miniaturized equipment, and facilitates development of small inexpensive instruments that can be more widely available for expression analysis.

The sensitivity and specificity of the instant miniarray invention is greatly enhanced by the GeneTAG technologies that improve sensitivity and quantification in expression array analysis by using a variety of DNA-based gene probe and reporter methods (Shafer, PCT WO-00-04192). The GeneTAG methods include an expression array based WRAP-Probe method wherein a pool of mRNA transcripts are globally converted into a pool of DNA-based WRAP-Probes that comprise short segments of cDNA copied from the original transcripts (see FIG. 4). The terminal ends of the WRAP-Probes are affixed with generic linkers. These terminal linkers are constructed with sequences that are not complementary to either the sample or to the array and they are designed to serve two alternate functions. Firstly, when these probes are helically coiled or wrapped around the cDNA targets on the chip after hybridization, the terminal linkers can very efficiently bind additional DNA-based reporters, called GeneTAGs, to the ends of the probes to amplify signaling. Secondly, the terminal linkers of the WRAP-Probes can also act as universal primer sites that enable unbiased global amplification of the entire set of probes by a modified version of PCR (FIG. 4). These methods and reagents would provide hundred fold to million fold increases in assay sensitivity.

The GeneTAG methods effectively concentrate the probe sample by either boosting signaling or by amplifying the probes themselves. Greater sample concentration enables dilution of the probes into a larger volume hybridization solution. Current microarrays, for example, typically populate a surface of 2 to 4 $cm^2$, and where the probe solution is enclosed by a coverslip, hybridization volumes are typically 10 to 30 microliters. However, if the probe concentration is effectively boosted just one hundred to two hundred fold, hybridization volumes can be readily increased to 500 to 1000 microliters and larger format glass or membrane miniarrays of 3 by 4 inches or 4 by 5 inches can easily be supported with no loss of sensitivity. Thus, the present invention can replace expensive microarrays with cheaper, larger format miniarrays with similar or equivalent diagnostic value. On the same basis, the methods of the present invention can also be used to create miniarrays on simple, small format substrates such as standard coated glass microscope slides, thereby enabling cheap and easy fabrication of low density custom miniarrays.

The most obvious value of the GeneTAG technologies for expression arrays is the advantage they convey in enabling the analysis of very small samples such as early stage cancer biopsies, micro dissections, small blood samples and archived tissue slices. Thus, samples too small for detection with current microarrays can be amplified or signal enhanced to a level where expression analysis can be completed. However, a less obvious but equally important advantage of these technologies is the potential they provide for reversing the reliance on miniaturized microarrays and high resolution scanning. Hundred fold to million fold increases in effective sample size enables the development of larger format miniarrays wherein: (1) the chips and spots can be larger and can have lower spot densities, (2) the scanners can be simpler and have less resolution, and (3) assay samples can be prepared with simpler and less expensive labeling. Overall, this new miniarray format would allow great reductions in cost and complexity—both for manufacturing arrays and for scanning them—without entailing significant reduction or change in assay sensitivity or quantification.

The instant miniarray system includes a spotter apparatus in which the spotter print head consists of one or more pipette tip holders arranged in a single row or multiple rows. The pipette tip holders can be electromechanically activated to aspirate or dispense nanoliter or microliter quantities of reagent solution into or out of the pipette tip(s) using sealed pistons or syringe pumps to vacuum in or pressure out the reagent solution. The print head is mounted on a mechanical or robotic arm that positions it laterally and vertically at precise locations in the array to load and dispense samples, or to clean or replace tips. The spotter print head can also mechanically eject and discard pipette tips as needed.

The present system also includes a miniarray support apparatus containing a series of processing stations accessible by the mechanical or robotic arm. These processing stations are places for affixing the miniarray substrates in precise locations via pins or trays, holding multi-well plates that provide reagent sample solutions, and loading, cleaning or discarding pipette tips. The spotter print head is devised in several versions: (1) the pipetter pistons are directly attached to the print head and are carried by the robotic arm, or (2) a set of stepper motor-activated syringe pumps are mounted on or adjacent to the working platform of the spotter and they are connected to the pipette tip holders on the print head by flexible microtubing.

The miniarray spotter can be fully robotic and driven by a computer program. Alternatively, the spotter operation can be largely mechanical and an operator powers or activates the steps of loading, spotting and tip cleaning or replacement. While the spotter print heads can be constructed with one pipetter or multiple pipetters, practical embodiments would have one or two rows of four to eight pipetters. Samples could then be readily loaded from standard 96 well or 384 well plates and spotted in a more condensed miniarray configuration by printing or spotting each successive sample loading at positions offset from and in between prior spottings.

For example, samples from a 96 well plate measuring approximately 3 inches by 4.5 inches could easily be spotted onto a coated microscope slide in a miniarray region of approximately 0.8 inches by 1.5 inches, wherein the spots would be spaced 3 mm CTC. If the spots are spaced 1 mm CTC, the same miniarray region would accommodate over 600 spotted genes. A larger region of about 5.5×7.5 cm would accommodate about 4000 spotted genes (FIG. 3). These miniarray spotters would thereby provide an inexpensive and reliable technology to create custom miniarrays on coated microscope slides that variably provide 20 to 600 spotted genes. Larger format miniarrays can be made on flexible membranes, rigid glass, plastics, semi-rigid film or paper-based printing substrates that provide many thousands of spotted genes. The use of semi-rigid printing materials, such as plasticized substrates used to make photographic film, photographic paper and high quality computer printing papers are uniquely enabled for miniarray applications by the features of this invention.

The present invention is also related to designs of miniarrays that are useful for diagnostic purposes. Present gene expression microarrays are generalized, multi-purpose assays wherein the pattern of spotting different genes is largely random or arbitrary. Complex, expensive and time-consuming software analysis must therefore be employed to relate and interpret the detected expression patterns to specific conditions or characteristics of the tissue evaluated by the assay. When custom microarrays are manufactured to target a more limited set of samples, such as inflammatory diseases, a subset of relevant genes are selected to populate the array and these genes may be arrayed in clusters of related genes. However, such microarrays have not been specifically designed and manufactured in their spotting pattern so that their final expression results would exhibit patterns that preferentially depict a single disease or condition. Therefore, complex, expensive and time-consuming software must still be employed to interpret these more limited, customized microarrays.

To overcome these limitations, the present invention provides novel diagnostic miniarrays that are specifically planned and spotted with disease or condition specific patterns built into their organization or arrangement. The presence of gene activity levels predicted for a specific disease, tissue or condition, such as up-regulated, down-regulated or unchanged activity levels, will create a simple recognizable clustered pattern in the array. These patterns are comparable to common visual images or patterns such as a stoplight, abstract symbols, simple pictures or alphanumeric characters Consequently, when the predicted disease or condition is present in the sample analyzed with such a miniarray, the planned visual pattern will emerge from the miniarray analysis as an easy to understand diagnostic indicator. This new diagnostic invention is enabled by the greater versatility and lower costs associated with the miniarray methods and devices disclosed herein. The advantage of this miniarray diagnostic design is that, by creating visually recognizable patterns in the miniarray, the process of identifying expression changes related to disease is greatly simplified without relying on complex computer algorithms. A doctor ordering such a diagnostic miniarray test would be able to intelligently review or participate in the analysis of the results without being trained as a microarray software expert, just like a general physician can interpret a patient's x-ray without additional training as a radiology specialist.

A person having ordinary skill in this art would recognize that the diagnostic miniarrays described above can have alternative configurations. For example, the visual pattern discerned can be created in the computer program which reads and displays the miniarray results so that the genes may still be spotted in an arbitrary manner. Nonetheless, the results displayed will automatically produce the intended diagnostic visual pattern in the array image if the predicted condition is present in the sample.

Moreover, diagnostic visual patterns can be created by spotting addressable generic probes on the miniarray that will form the identifying pattern indirectly. In this embodiment of the present invention, expression levels are actually assessed by binding probes to the sample in solution hybridization, employing conditions that create a probe set which represents the gene frequency levels of the sample. An addressable miniarray is then employed to capture and represent the probe set, thereby displaying the diagnostic visual pattern if the disease or condition assayed is present. The generic capture probes spotted on the miniarray can consist of: 1) synthetic oligonucleotides or artificial DNAs (PNA) that form unique sequence addresses at unique locations or sets of similar sequence addresses at multiple locations; 2) selected hapten binding elements at unique or multiple locations; or 3) selected antibodies at unique or multiple locations. Representative gene probes that bind to samples are generally made of synthetic oligonucleotides with two principal forms. Firstly, the probes can be singular probes having a miniarray address-binding sequence, a target-binding sequence, and a label or label-binding region. Alternatively, the probes are constructed from two half-probes. The first half-probe element contains a miniarray address-binding sequence and a partial target-binding sequence, whereas the second half-probe element has a label or label-binding region and a partial target-binding sequence that binds to sequence adjacent to that bound by the first half-probe. These half-probes are brought in proximity and ligated together by virtue of binding in tandem to the full target sequence, thereby forming a single probe unit containing both a miniarray address and a label or labeling potential. Once the target sequence is removed or degraded, effective detection can result due to the fact that the probe allows the reporter potential to be captured by the miniarray at a preplanned address. The two half probe system additionally confers greater target specificity since the reporter potential is lost if precise target-specific ligation does not occur. With all of these methods, diagnostic miniarray patterns are thus determined beforehand by planning which target specific probe will be joined to which capture address on the array The diagnostic miniarray pattern inventions described above have general diagnostic characteristics which can be extended to other expression analysis formats, such as high or low density microarrays, wherein such assays would likewise be designed and created so that simple visual patterns will similarly emerge in the array image if the predicted diagnostic condition is present.

The present invention is drawn to a system for dispensing nanoliter-sized droplets on a surface in a precise pattern of non-overlapping spots to form a two dimensional miniarray assay. The system includes (1) a spotter device comprising a print head for making said miniarray assays, wherein said print head comprises pipette-based dispensers, (2) a robotic or mechanical arm carrying the print head, and (3) a working platform containing regions or substations for holding miniarray substrates, loading samples and tips, and for cleaning or discarding tips. Generally, the print head contains one or two rows of pipetters that can operate simultaneously to load microliter quantities of sample analyte reagents in solution and to dispense nanoliter quantities of said reagent solutions on the surface of the miniarray substrate. The pipetters can have disposable tips that can be ejected and replaced automatically, or have fixed tips that are cleaned and dried between sample loadings. The spotting function of the print head may be actuated by remote syringe pumps that provide vacuum or pressure to the pipetters via a set of flexible airtight microtubes, or mechanically activated by minute pistons that are fixed to each pipetter of the print head, or the print head may have pipetter pistons that are hydraulically actuated by remote syringe pumps.

The present invention is also directed to a method for forming miniarrays where each known location or spot in the array contains analyte specific reagents for detecting analyte samples The method involves aspirating a solution of each analyte specific reagent with a controlled volume pipetting device that has one or more coordinated pipette dispensers. These pipette dispensers have disposable or washable pipette tips, and they have the capacity to load microliter quantities or less of a reagent solution and to dispense nanoliter quantities or less of said reagent solution. The tips of these pipette devices can be replaced or cleansed before reloading the tips with new reagent solution. The pipetting device can be carried by a robotically controlled apparatus that provides lateral and vertical motions, thereby automating the loading of multiple reagent samples, the replacement or cleaning of pipette tips, and the spotting of multiple miniarrays under programmed instructions. In another embodiment, the pipetting device is stationary, except for vertical motion, and the device includes a robotic apparatus that moves the miniarray substrates and the reagent samples under the pipetting device as needed under programmed instructions.

An individual pipetter used in the above method is capable of pressuring a small defined droplet of the reagent solution from the narrow opening of the tip, and touching the droplet to the surface of the miniarray substrate with an action effective to release each drop, thereby spotting a specific location in the array with a specific volume of each reagent. A defined drop of reagent solution can be released by gravity and controlled by the size of the pipette tip or by the addition of electromechanical force to vibrate or squeeze the pipette tip. Representative miniarray substrates include coated microscope slides, flexible membranes, rigid glass, plastics, semi-rigid film, paper-based printing substrates, semi-rigid printing materials, photographic paper and high quality computer printing papers.

The above method can form a miniarray with a smaller and more condensed distribution by interspersing successive dispensing of reagents onto the array in regions between the spots dispensed previously. In one embodiment of the above method, multiple tips of the pipetting device are spaced to load multiple reagent samples from standard sample plates such as 96 well or 384 well plates, wherein the wells are typically spaced 9 mm CTC (center to center) or 4.5 mm CTC respectively.

In general, analyte specific reagents dispensed by the above method include polynucleotides or synthetic oligonucleotides complementary to sequences of the analyte sample, antibodies that bind to selected proteins of the analyte sample, as well as cloned or amplified cDNAs or synthetic oligonucleotides containing sequences that are matching or complementary to the mRNA sequences of the analyte sample in order to detect and measure the relative frequency with which specific genes are expressed in the sample.

In general, analyte samples detected by the above method include total RNA, mRNA, cDNA probes made from RNA transcripts, intracellular proteins or secreted proteins. Two or more analyte samples can be compared by competitive binding to the same miniarray. The samples can be differently labeled by isotopes, indirect labeling haptens, direct fluorescent reagents, indirect fluorescent reagents, quantum dots or nanogold.

The present invention is further directed to a method of diagnosis for specific tissues or conditions using custom or specialized miniarrays targeted to the analysis of these conditions. Such conditions include but are not limited to cancer and disease states, responses to specific infections, responses to a specific therapeutic or toxic drugs or agents, or stages of development or aging. The method involves arranging on a miniarray gene specific elements (ranging from 10 to 1000, or from 50 to 300) that correspond to genes known to be significantly up-regulated or down-regulated in the targeted tissue or condition relative to control sample, as well as a selected sampling of gene specific elements that represent tissue-specific or housekeeping genes not known to be up-regulated or down-regulated in the condition evaluated. Detection of a visually distinct image from said miniarray indicates the presence of said tissue or condition. Gene specific elements such as amplified cDNAs, cloned cDNAs, synthetic oligonucleotides and PNAs (proteins manufactured to mimic nucleic acid segments) can be used to detect target sample containing expressed RNAs or nucleic acid copies thereof, whereas a selected subset of specific antibodies can be used to detect samples of expressed proteins.

The distinctive visual patterns or signatures are simple and easy to recognize images that include, but are not limited to, well known images such as a stoplight or other common objects, abstract signs, shapes and symbols, alphanumeric characters, and simplified pictures representing organs or conditions. Representative symbols include triangles, rectangles, squares, circles, ovals, trapezoids, stars, hexagons, pentagons, octagons, bars, stripes, squiggles, rings, mathematical symbols, language symbols, as well as the shape of a lung, heart, brain, kidney, stomach, breast, colon, a ragged rough-edged cell, a smooth round cell, etc. These patterns are distinguished by differences in color, intensity or location within the miniarray.

These specialized miniarrays are manufactured with a selected set of gene transcript identifiers that are intentionally organized and/or arranged in a particular manner based upon the predicted gene activity levels characteristic of the targeted disease, tissue or condition. The gene spots are planned and arranged so that if the targeted disease or condition is present, the miniarray will exhibit a distinctive visual pattern or signature that serves as a simple diagnostic fingerprint for that particular disease or response in question. For example, gene specific elements corresponding to up-regulated genes, down-regulated genes and unchanged genes can be clustered in separated groups. Alternatively, gene specific elements are not clustered into specific groups on the miniarray, and the visually distinct image is generated by computer means.

The present invention is also directed to methods of diagnosis for a specific tissue or condition using specialized diagnostic miniarrays that involve binding sets of intermediate probes to target samples in solution hybridization conditions. The intermediate probes contain a specific binding element that binds to a specific gene expression product in a target sample and a generic binding element that binds to a matching binding element spotted on an addressable miniarray. After the unbound intermediate probes and target sequences in the samples are removed, the remaining intermediate probes are applied to the miniarray that is spotted with different binding elements. Subsequent detection of a visually distinct image from said miniarray indicates the presence of the tissue or condition. Representative conditions which can be analyzed by this method of diagnosis and examples of visually distinct images are the same as described above.

The intermediate probes used above also contain reporter elements such as direct labeling agents, indirect label-binding molecules, haptens, or linker sequences that can bind a separate reporter such as labeled DNA, GeneTAGs or ChipTAGs. These reporter elements or reporters are bound to the intermediate probes before or after said intermediate probes are bound to the miniarray.

The intermediate probes can be constructed in different ways. In one embodiment, the intermediate probe comprises two half-probes. The first half-probe contains a first binding element that binds to a first sequence in a target sample and a binding element that binds to a matching binding element spotted on the miniarray. The second half-probe contains a reporter element and a second binding element that binds to a second sequence in the target sample. The first sequence and the second sequence are adjacent sequences in the target sample and the first half-probe and the second half-probe are joined together to form a singular unit by a ligase enzyme after binding to the target.

In another embodiment, the intermediate probes are constructed as WRAP-Probes with universal linker/primer sequences at both ends, wherein increased signaling can be obtained by binding additional reporters to said universal linkers or exponentially amplifying said intermediate probes with a single primer set matching said primer sequences.

The binding elements printed on the addressable miniarray can also be constructed in different ways. In one embodiment, the binding elements are generic oligonucleotides that are not substantially complementary to sequences of the target sample and that constitute an arbitrary set of unique addresses and unique locations on the miniarray. The binding elements on the miniarray can be organized in pre-defined patterns to facilitate the creation of said visually distinct image.

In another embodiment, the miniarray is printed with a small subset of binding elements that create different common capture areas on the miniarray to form a visually distinct image, whereas the intermediate probes are grouped into different groups that each has a common binding element which binds to a matching binding element spotted on the miniarray. These groups of intermediate probes are designed to detect expression of genes that are up-regulated, down-regulated or unchanged in the tissue or condition under investigation. In general, the binding elements printed on the miniarray can be generic oligonucleotides, antibodies or other affinity ligands including but not limited to avidin, streptavidin and antibodies to digoxygenin, fluorescein dinitrophenyl, nitrotyrosine, tetramethylrhodamine, Texas Red, dansyl, Alexa Fluor 488, BODIPY Fla., lucifer yellow, Cascade Blue and Marina Blue, whereas the matching binding elements on the intermediate probes are complementary linker sequences, haptens or other ligands including but not limited to biotin, digoxygenin, fluorescein, dinitrophenyl, nitrotyrosine, tetramethylrhodamine, Texas Red, dansyl, Alexa Fluor 488, BODIPY Fla., lucifer yellow, Cascade Blue and Marina Blue.

The following examples are given for the purpose of illustrating various embodiments of the invention and are not meant to limit the present invention in any fashion.

EXAMPLE 1

Miniarray Fabrication

Figure 5:
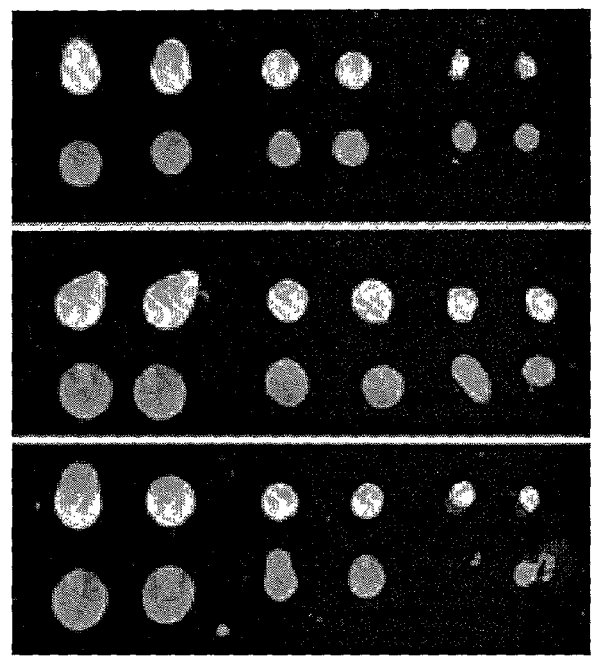
FIG. 5 shows a test sample of hand spotted miniarray distributions using a P-10 model Gilson micropipetter. The spots were dispensed on polylysine coated microscope slides and were read with an Affymetrix 418 Array Scanner. The green spots contained Cy3 fluorescent reagents and the red spots contained Cy5 fluorescent reagents. The spot size relative to the volumes dispensed indicate that useful miniarrays can be created with micropipetter devices, particularly volumes of 200 nanoliters or less can be reliably dispensed.

Typically, electronic or mechanical controls activate the operations of the print head and enable it to be moved laterally and vertically in relation to the functional regions of the working platform. The loading of each pipette tip is achieved by a mechanical pump or piston that aspirates the liquid sample by vacuum, typically drawing 2 to 20 microliters per pipetter. Dispensing is controlled by first applying minute pressure on the piston to form a droplet of reagent on the pipette tip and secondly by touching said droplet to the surface of the miniarray substrate. Alternatively, the piston may be plunged sufficiently to pressure a droplet from the pipette tip until the droplet releases by gravity (see FIGS. 1). While air-based micropipetters are not effective in aspirating solution quantities of less than half a microliter, hand-controlled pipetters can be demonstrated to load microliter quantities and to dispense nanoliter quantities in the range of 200 to 50 nL by capillary action (see FIG. 5). Thus, such pipetters can be effectively employed in a printing function.

With precise, commercially sold syringe pumps, pistons 20 mm long with a bore of 1.2 mm will load approximately 20 microliters of sample and can dispense 100 aliquots of 200 nanoliters each. Pistons 15 mm long with a bore of 1 mm will load approximately 10 microliters of sample and can dispense 100 or more aliquots of 100 nanoliters or less. Small stepper motor-activated syringe pumps can employ different capacity syringes ranging from 50 microliters to 25 milliliters and they can achieve 2000 to 3000 steps of resolution in a 30 mm stroke. Such pumps are readily available from commercial vendors such as Cavro or Gilson. Therefore, when mounted with 50 microliter syringes having 3000 steps of resolution, the syringe pump-based pipetters can dispense aliquots as small as 17 nanoliters from each pipette tip to spot the miniarrays.

The working platform contains mechanical devices and regions for holding array substrates in known, fixed positions, for holding plates of samples to be dispensed, and for holding racks of disposable tips or discard trays. In one embodiment of the device, the spotting region of 7 by 13 inches will hold up to 20 microscope slides of 1 by 3 inches or up to 6 larger format substrates of 3 by 4 inches for a single print run. This embodiment will also hold one or two 96 or 384 well plates with reagent samples and 1 or 2 racks of disposable pipette tips (see FIG. 2). Robotic embodiments of the invention include electromechanical devices that move and operate the print head and a computer controller and software that programs the device and records the microarray location of each analyte sample. These robotic arms and controlling software are readily available from commercial vendors, such as Gilson, Tecan, Cavro and Qiagen, although these devices have not been specifically developed for miniarray manufacture.

When the device is automated and uses disposable pipette tips, the working platform is first loaded with array substrates, plates of reagent samples in solution, racks of pipette tips, and a discard tray. The automated sequential operations are as follows: (1) first loading pass—move the print head to the pipette tip rack, load a set of tips, move the print head to the sample plates, load the first set of samples, typically four or eight pipetters loaded per pass; (2) first printing pass—move the print head to the upper left corner of the first array substrate, spot nanoliter aliquots of the reagent samples to that array substrate, repeat this operation for the remaining array substrates, move the print head to the discard tray and eject the used pipette tips; (3) second and subsequent loading and printing passes—repeat step (1) with the second or subsequent samples, and repeat step (2) by advancing the location of the print head on each array by one increment, moving down and/or right of the first pass location on the array to defined intermediate positions that do not overlap prior printing positions. The distance and direction of each printing pass are set and recorded by a predefined program.

Reagents are loaded and dispensed in a predetermined grid to create a condensed miniarray of the reagents employed. When the print head contains one or more rows of pipetters, the pipetters are arranged to pick up sample solutions from a row of wells in a standard plate, such as 96 or 384 well plates which are typically spaced 9 mm CTC or 4.5 mm CTC. A print head with two rows of four pipetters spaced 9 mm CTC will deposit eight droplets on the first pass in a region of approximately 9 mm by 27 mm. Depending on the size of the droplets dispensed and the density intended, successive passes are set to dispense droplets in regions which offset the first pass by small increments to achieve a more condensed array pattern on the substrate vs. the spacing of the print head tips (see FIG. 3). Simple low density miniarrays are made by offsetting each printing pass by 3 mm CTC. to achieve miniarrays on microscope slides with 64 spots in a small region 18 mm by 36 mm, or 96 spots in a region 24 mm×40 mm. If smaller droplets are arrayed with the same print head, using smaller 1 mm offsets CTC, a miniarray of 648 spots is achieved in a 18 by 36 mm region with 81 printing passes. Higher density miniarrays offset by 0.5 mm (500 microns) CTC can achieve about 1000 spots on a microscope slide and about 22,000 spots on a 3 by 4 inch miniarray.

The present invention may be used in a variety of situations to produce miniarrays, to dispense cell samples or test solutions, to process multi-well plates, or the like. The dispensed solutions may contain multiple components, including single compounds, oligomers or polymers, natural or synthetic substances, reagents that are chemically reactive or unreactive. The present invention may be used to mix, combine or chemically join various compounds or reagents. In addition, multiple reagents may be brought together in different combinations at different positions within the array in order to determine the individual contribution of various agents to such reactions.

Expression miniarrays can be created wherein the spotted analyte reagents consist of synthetic DNA oligonucleotides, RNAs or PNA samples and not just samples of different cDNAs. Furthermore, expression miniarrays can also be created with the present invention based upon printing samples of protein specific antibodies and then applying a labeled protein sample to the array to determine the frequency of expression of the assayed proteins within the sample. Antibody printing can be performed with standard microarray instruments on glass slides coated with poly-L-lysine, nitrocellulose or aminosilane. Consequently, miniarrays can be made for a variety of screening and diagnostic purposes in addition to uses for research purposes. These arrays may involve two or more printing steps wherein the first printing pass provides a set of reagents and the second or subsequent printing passes deposits a second or additional sets of reagents within the same location to determine binding, hybridization, chemical reactions, or the like. Such miniarray assays would indicate the presence, absence or concentration levels of specific components in the test samples. These miniarray detection or measurement operations may include one or more washing steps, intermediate reaction steps, or labeling steps in order to achieve diagnosis, analysis or the like.

The array substrates to which the droplets are dispensed may take many forms, depending on the nature of the substrate material and on the purpose of the array. The substrate may be chemically active or the like so that the reagents dispensed become bound or joined to it through electrostatic attraction, covalent bonding and the like. In the case of expression miniarrays, a coated array substrate, such as polylysis coated microscope slides, could be spotted with samples of different cDNAs or oligonucleotides representing different gene transcripts such that these samples become firmly bound to the substrate. A test sample of labeled aRNAs or cDNAs can then be applied in liquid solution to determine the hybridization of said aRNAs or cDNAs to the spotted analyte positions on the miniarray. After unbound test sample is removed by washing, the pattern of the sample remaining may define the tissue origin or pathology of the test sample, the presence of infectious agents or reactions thereof, the diagnosis of neoplastic tissue, the cellular reaction to drugs, chemicals or environmental reagents, the prognosis for the disease or its treatment.

EXAMPLE 2

Diagnostic Miniarrays

The present invention also relates to methods wherein the miniarrays are designed on the basis of disease-specific gene expression patterns that are predicted from clinical information or prior expression studies. Prior art has demonstrated that two tissues can be compared by competitive two-color probe binding to the same microarray, wherein expression changes in the subject sample will produce distinct color shifts in individual gene spot depending on whether the activity of that gene is increased or decreased.

Figure 6:
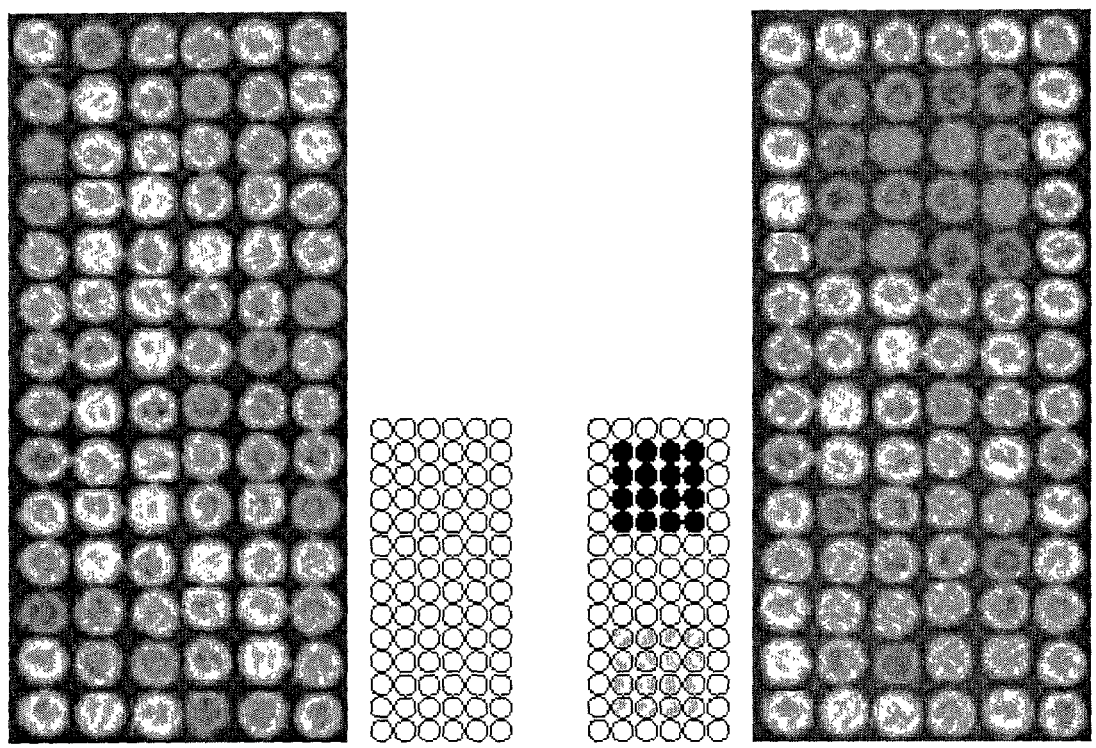
FIG. 6 shows schematic representations of small diagnostic miniarrays with the genes of the arrays arranged in a disease specific pattern. The presence of a disease, e.g., a particular cancer, will cause clustered patterns of up- and down-regulated gene activity reflected as regions of differential brightness and color that form a simple image such as a traffic stoplight in the miniarray. As compared to the sample on the left without the predicted disease state, the miniarray sample on the right fits the diagnostic test for the cancer or disease by showing a stoplight pattern in the miniarray with three vertical clusters of gene spots that are predominantly labeled red, yellow and green from top to bottom and those clusters are surrounded by gene spots that are predominantly labeled yellow. The diagnostic miniarray patterning pre-selected for each disease-specific assay is usually based upon using red fluorescent labeling for the cancer or diseased sample and green fluorescent labeling for the normal tissue sample. No change in gene activity will yield a mixed yellow to brown color; disease activation of a gene yields a shift to red; whereas disease inactivation of a gene yields a shift to green for that spot. The smaller image patterns shown between the larger schematic miniarray images show the expected and planned visual image of the miniarray if the disease or condition is not present (left pattern), or if the disease or condition is present (right pattern). Alternate labeling and pre-designed simple patterns could be employed for alternate disease-specific miniarrays.

Exploiting these induced signaling differences, the diagnostic miniarrays of the present invention are structured to form visual patterns in the miniarray based on clustering together groups of gene spots that are either upregulated, downregulated or unchanged in the disease state as compared to normal tissue of the same origin. One such embodiment is to arrange such miniarrays for a particular disease in a stoplight pattern wherein the upregulated genes will show an upper red cluster, the unchanged genes will show a mid level yellow cluster and the downregulated genes will show a lower green cluster. Other unchanged genes may be arrayed surrounding the red, yellow and green clusters. When the disease or condition is not present, such miniarrays will yield an essentially flat image without such visual distinction (see FIG. 6). These disease-specific miniarrays may use the same genes or different genes in each disease-specific design with the emphasis on achieving a similar visual pattern with each such miniarray despite the differences that may exist in gene expression levels for each specific disease.

Alternatively, this invention may use other simple images such as vertical or horizontal stripes of different colored gene spots vs. rectangular or circular clusters. In addition, alternate simple images could indicate each disease with a different signature pattern. For example, the diagnosis of lung cancer with a lung cancer specific miniarray could yield a pattern of red spots forming the letter L and an adjacent pattern of green spots forming the letter C if the disease were present, whereas for breast cancer the expression patterning would form a red B and a green C, and so on.

Other examples of miniarray visual patterns include but are not limited to the use of abstract symbols and shapes such as triangles, rectangles, squares, circles, ovals, trapezoids, stars, hexagons, pentagons, octagons, bars, stripes, squiggles, rings, mathematical and language symbols, etc. For example, the letters "LCa" can designate lung cancer, "ALL" for acute lymphocytic leukemia, etc. These shapes and symbols may be distinguished by differences in color or intensity as well as their location within the miniarray. Furthermore, miniarray visual patterns could include small pictures or symbols representing targeted tissues or conditions, such as the shape of a lung, heart, brain, a ragged rough-edged cell vs. smooth round cells, etc.

Some of these diagnostic miniarray fingerprint patterns can be used repeatedly with different miniarrays representing different conditions. Alternatively, different miniarray patterns or images are employed for each condition or tissue. For example, a stoplight pattern could be employed repeatedly for multiple miniarrays targeted to different cancer states or tissues, but for each different miniarray for each different tissue or cancer state, a different set of genes are included in each gene cluster to make up the up-regulated, down-regulated and unchanged genes. Moreover, the stoplight pattern for different diagnostic miniarrays could be significantly different in visual patterning within the colored clusters such that lung cancers versus spleen cancers are likely to have distinct and recognizable variations in intensity within each colored cluster that relate particularly to the expression behavior of each disease.

Figure 7:
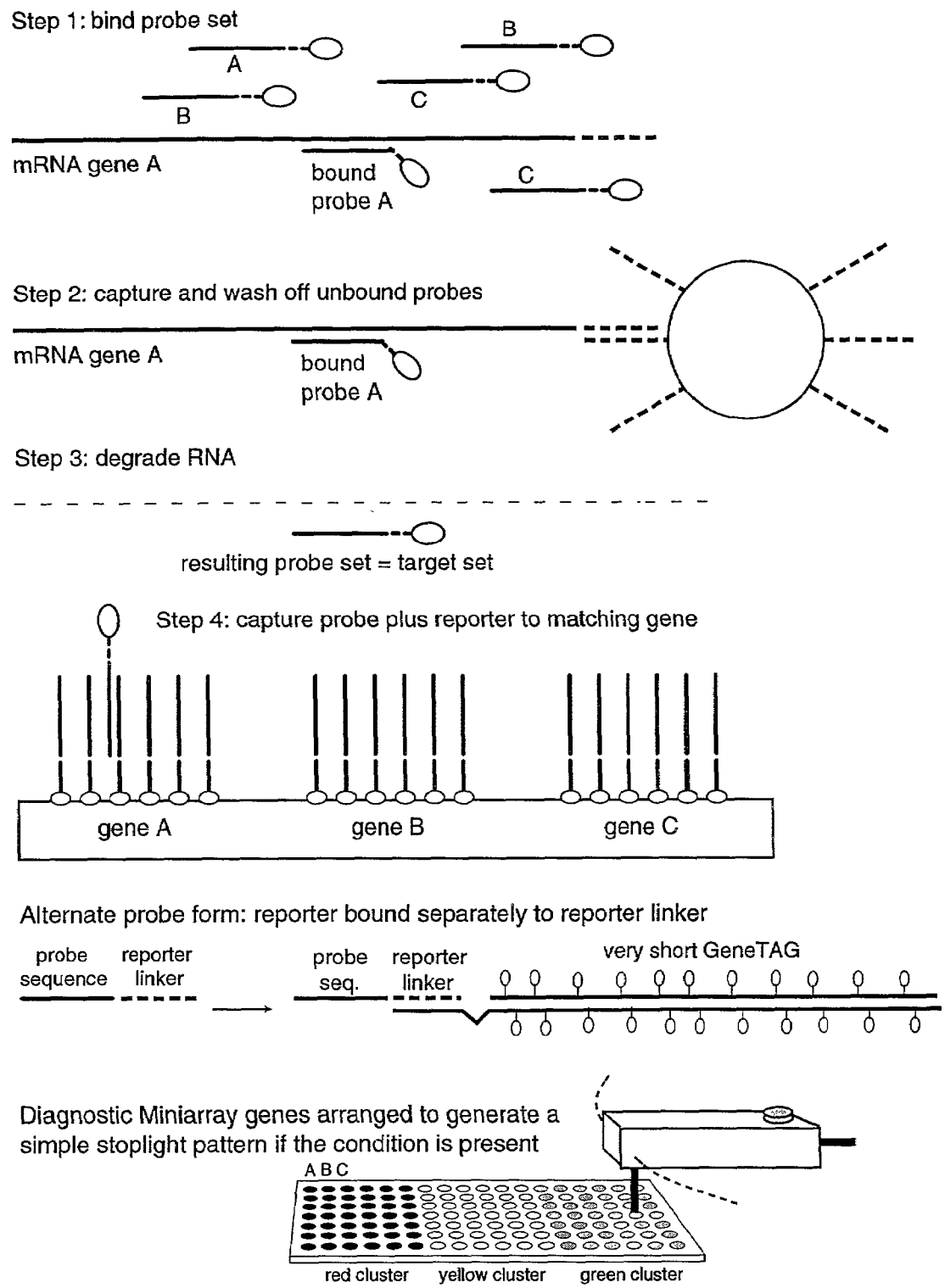
FIG. 7 shows the design and application of diagnostic miniarrays wherein the gene-specific elements of the array are intentionally arranged in clustered patterns that will produce a visually distinct signaling image if the predicted disease or condition is present. This illustration depicts the use and method of employing a pre-made set of labeled synthetic oligonucleotide probes that selectively bind to the subset of genes employed in the miniarray. The probes employed are further selected by a capture and wash step (step 2) to produce a subset of oligoprobes that represents the expression frequencies of that gene set within the sample tested. The resulting probe set is then applied to the miniarray wherein they would bind to matching oligonucleotides on the array and provide signaling proportion to expression frequencies. The arrays are scanned for color and intensity to produce a visual pattern deemed diagnostic of the condition. Alternatively, the probes are not labeled beforehand but receive labeling by binding generic reporters such as GeneTAGs to a generic labeling segment or linker added onto each probe.

The diagnostic fingerprint or image desired can be produced by different procedures. The desired image can be produced according to the physical placement of the gene spots in a pre-defined miniarray pattern (see FIG. 7). Alternatively, the gene spots can be placed arbitrarily on the miniarray, but those gene spots occupy planned locations in computer memory files of the miniarray that correspond to the disease or condition specific arrangement required to produce the diagnostic visual pattern.

Figure 8:
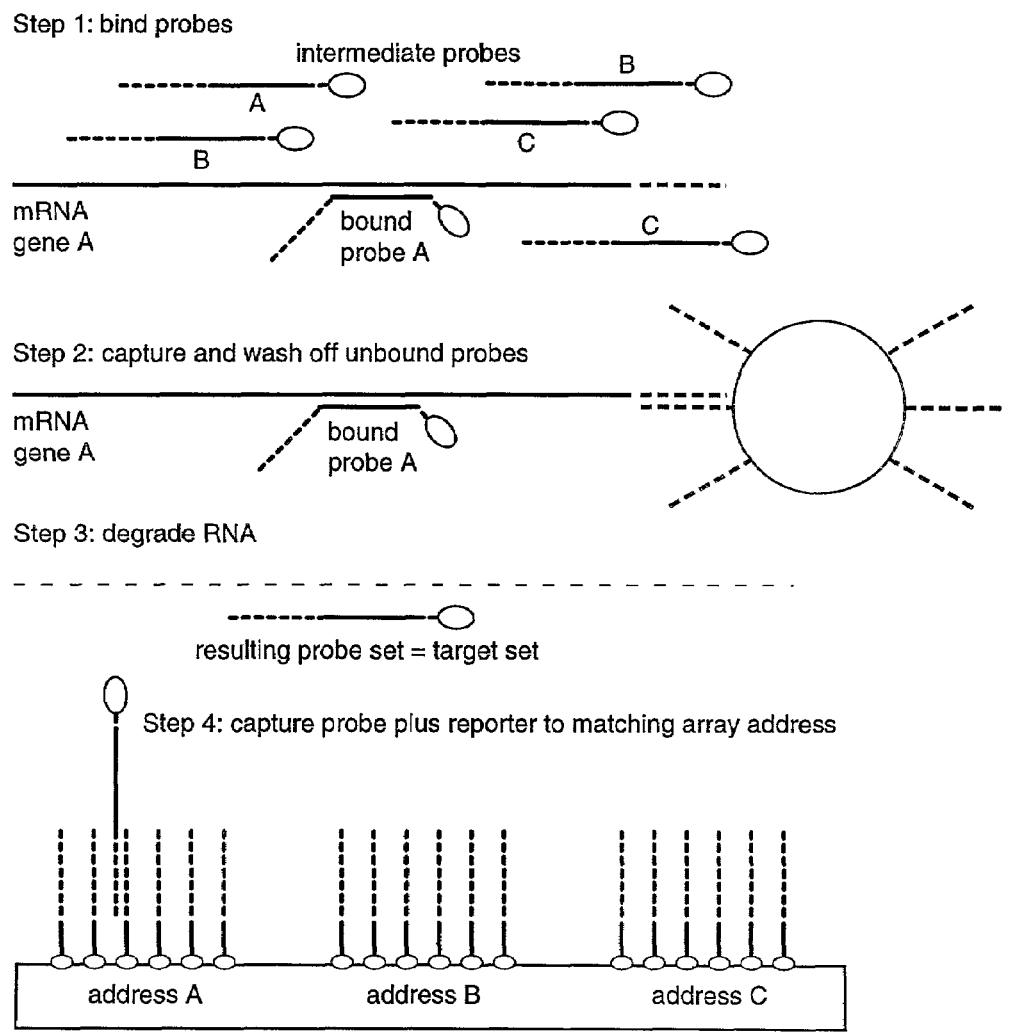
FIG. 8 shows the design and method of using addressable diagnostic miniarray which is spotted with generic probes not complementary to the target sample. Each probe spotted on the array constitutes a sequence address for capturing the expression probe set. A number of intermediate probes are constructed that recognize and bind to specific expression products in proportion to their frequency in the sample. These intermediate probes have a generic sequence tail corresponding to a miniarray sequence address. After the intermediate probes are applied to the sample, captured and washed, the resulting subset of intermediate probes is bound to the miniarray via the address tails and provides signaling proportional to expression frequencies. A distinct visual pattern shown in the array identifies the condition and or tissue analyzed.

The predicted diagnostic visual image can also be produced by spotting a miniarray with generic capture probes in a particular pattern of addresses. When a labeled probe set binds to these capture probes, the predicted diagnostic visual image will emerge if the disease or condition is present. In one embodiment, the generic capture probes spotted on the array consist of synthetic oligonucleotides that are not complementary to the target sequences and constitute a series of different sequence addresses with similar binding characteristics. These capture probes will bind synthetic intermediate probes that carry addressable tails or segments that bind the intermediate probes to specific capture probes on the miniarray. These intermediate probes are also targeted to a target sequence in the sample. Hence, the miniarray signature pattern is created by the arrangement of the addressable capture probes on the array and by deciding which gene-specific intermediate probe will be associated with which array-specific address (see FIG. 8).

In another embodiment of this method, the intermediate probe is constructed from two half probes, one with address-specific capture potential and one with label or signaling potential. The paired half probes specifically bind to adjacent sites on the same gene target, and they will then be fused into one unit by ligase enzyme, thus joining the capture potential to the reporter potential (see FIG. 9). This method confers additional specificity in recognizing a precise target, although at the cost of a supplemental processing step. The end result is the same as the method using single intermediate probes in that the ligated half probe brings the signaling or reporter potential of the probe into contact with the capture address on the miniarray.

In yet another embodiment for the addressable diagnostic miniarrays, the capture probes on the miniarray consists of a small number of different capture probes that are arranged in particular clusters, symbols or images. Each of these capture probe type may bind probes from multiple specific genes that share a common addressable tail. In this embodiment, for example, the gene group selected to represent up-regulated genes for the condition or disease will create an area or shape in the array of relatively uniform intensity and color since all genes in that group could bind randomly to each spot in that area or shape. This variation would mute specific gene differences in intensity, but would simplify the patterning and manufacture of the miniarray. An intermediate level of diagnostic specificity could be retained by subdividing the gene clusters of upregulated and downregulated genes into levels or subclasses of said clusters. The simplified miniarray could then be populated with a more diverse set of capture probes on the array, thereby giving some distinction based on relative changes in expression between genes.

In still yet another embodiment, a small set of anti-hapten antibodies is employed to capture the probes of different gene sets to the miniarray in a defined pattern. For example, biotin, digoxygenin and fluorescein could be employed as haptens incorporated into the gene specific probes; wherein each hapten would be selected to represent the up-regulated, down-regulated and unchanged genes diagnostic of a particular tissue or condition. Probes from each subset would then bind randomly to their respective antibodies spotted on the miniarray in a defined signature pattern.

All of the above described diagnostic miniarray methods would have enhanced sensitivity and processing speed due to the fact that they employ solution hybridization conditions versus surface-phase hybridization conditions in the critical step of recognizing and binding gene specific probes to the expression products of the sample. The recognition and binding process is restricted and slow in standard microarray methods that are dependent upon surface-phase hybridization conditions. Hence, the diagnostic miniarray methods described above are expected to improve the speed and diagnostic value of miniarray expression analysis.

The following references were cited herein:

DeRisi et al., Nature Genetics, 14: 457–60, (1996).
Duggan at al., Nature Genetics, 21: 10–14 (1999).
Fodor at al., Science, 251:767–773 (1991).
Hailer at al., Proc. Nati. Acad. Sci., 94: 2150–5, (1997).
Khan et al., Cancer Ret. 58: 5009–13 (1998).
Khan at al., Electrophoresis, 20: 223–9 (1999).
Khrapko at al., DNA Sequencing and Mapping, 1:375–388 (1991).
Lehrach at al., "Hybridization Fingerprinting in Ganome Mapping and Sequencing," in Genome Analysis, vol. 1: Genetic and Physical Mapping. (Davies & Tilgham, Eds.) Cold Spring Harbor Lab. Press, pp. 39–81 (1990).
Liang at al., Nucleic Acids Rae., 21: 3269 (1993).
Mou et al., Siochem. Biophys. Rae. Comm., 199: 584–569 (1994).
Phillips at al., Methods, 10: 283–288 (1996).
Rajeevan at al., Jour. Histochem. Cytochem., 47: 337–42 (1999).
Schana at al., Science, 270: 467–470 (1995).
Schena, at al., Proc. Ned. Aced. Sci., 93:10614–9 (1996).
Shalon at al., Genome Rae., 6: 639–45 (1996).
Southern at al., Ganomics, 13:1008–1017 (1992),
Welsh at el., Nucleic Acids Res., 18: 7213–18 (1990).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for forming a miniarray on a miniarray substrate, said miniarray comprising locations or spots that contain an analyte specific reagent for detecting an analyte in a sample, said method comprises the steps of:

(a) aspirating a solution of each analyte specific reagent into dispensers comprising pipette tips spaced 9 mm or 4.5 mm center to center to load multiple reagent samples and said dispensers connected to a syringe pump;

(b) pressuring nanoliter quantities of defined droplets of said analyte specific reagent from the pipette tips of said dispensers that has been loaded with microliter quantities of said analyte specific reagent;

(c) touching said droplets to said miniarray substrate and causing said droplets to release through gravity which is perfomed by applying an electromechanical force to the tips of said dispensers, thereby spotting specific locations or spots on said substrate with a specific volume of said analyte specific reagent, wherein said locations or spots have a center-to-center spacing of in the range of 1 mm to 3 mm; and (d) repeating steps (a) to (c) until said miniarray is fabricated.

2. The method of claim 1, wherein said dispensers are arranged in one or two rows.

3. The method of claim 1, wherein said dispensers have disposable tips that can be ejected and replaced automatically or fixed tips that are cleaned and dried between sample loadings.

4. The method of claim 1, wherein causing said droplet to release through gravity is performed by increasing pressure on said defined droplet to eject sufficient volume from the tips of said dispensers to cause said droplet to release by gravity.

5. The method of claim 1, wherein causing said droplet to release though gravity is performed by applying an electromechanical force to the tips of said dispensers to cause said droplet to release by gravity, wherein said electromechanical force is selected from the group consisting of vibration, piezoelectric pressure, and rapid mechanical actuation.

6. The method of claim 1, wherein said dispensers are carried by a robotically controlled apparatus that provides lateral and vertical motions, thereby automating the loading of multiple reagent samples, the replacement or cleaning of the pipette tips, and the spotting of multiple miniarrays under programmed instructions.

7. The method of claim 1, wherein said miniarray achieves a smaller, more condensed distribution by interspersing successive dispensing of reagents onto the array in regions between the spots dispensed previously.

8. The method of claim 1, wherein said dispensers are stationary, except for vertical motion, and miniarray substrates and reagent samples are moved under said dispensers by a robotic apparatus.

9. The method of claim 1, wherein said miniarray substrate is selected from the group consisting of coated microscope slides, flexible membranes, rigid glass, plastics, semi-rigid film, paper-based printing substrates, semi-rigid printing materials, photographic paper and high quality computer printing papers.

* * * * *